(12) United States Patent
Slater et al.

(10) Patent No.: US 6,562,208 B2
(45) Date of Patent: May 13, 2003

(54) GAS SENSORS

(75) Inventors: Cody Zane Slater, Alberta (CA); John Robert Finbow, Hampshire (GB)

(73) Assignee: BW Technologies Limited, Calgary (CA)

( * ) Notice: Subject to any disclaimer, the term of this patent is extended or adjusted under 35 U.S.C. 154(b) by 13 days.

(21) Appl. No.: 09/902,650

(22) Filed: Jul. 12, 2001

(65) Prior Publication Data

US 2002/0036137 A1 Mar. 28, 2002

(30) Foreign Application Priority Data

Jul. 14, 2000 (GB) .............................................. 0017246

(51) Int. Cl.[7] .............................................. G01N 27/404
(52) U.S. Cl. ........................................ 204/401; 204/415
(58) Field of Search ................................... 204/401, 415

(56) References Cited

U.S. PATENT DOCUMENTS

RE31,914 E * 6/1985 Oswin et al.
4,633,704 A 1/1987 Tantram et al.
5,273,640 A * 12/1993 Kusanagi et al.

FOREIGN PATENT DOCUMENTS

| EP | 0 216 623 | 11/1984 |
|---|---|---|
| GB | 1 571 282 | 7/1980 |
| GB | 1 572 282 | 7/1980 |
| GB | 2 094 005 | 9/1982 |

OTHER PUBLICATIONS

"Techniques and Mechanisms in Gas Sensing" by B.S. Hobbs, ADS Tantram, R. Chan–Henry, editors P.T. Moseley, J. W. Norris, and D.E. Williams, 1991 (ISBN No. 0–7503–0074–4) pp. 161–188.

* cited by examiner

Primary Examiner—T. Tung
(74) Attorney, Agent, or Firm—Burns, Doane, Swecker & Mathis, L.L.P.

(57) ABSTRACT

A combined toxic gas sensor and an oxygen sensor includes a sensor body 1 with a top plate 2 provided with a toxic gas diffusion barrier 3 leading to a chamber 7 from having an outlet aperture 5 registering with the diffusion barrier 6 of the oxygen sensor.

9 Claims, 1 Drawing Sheet

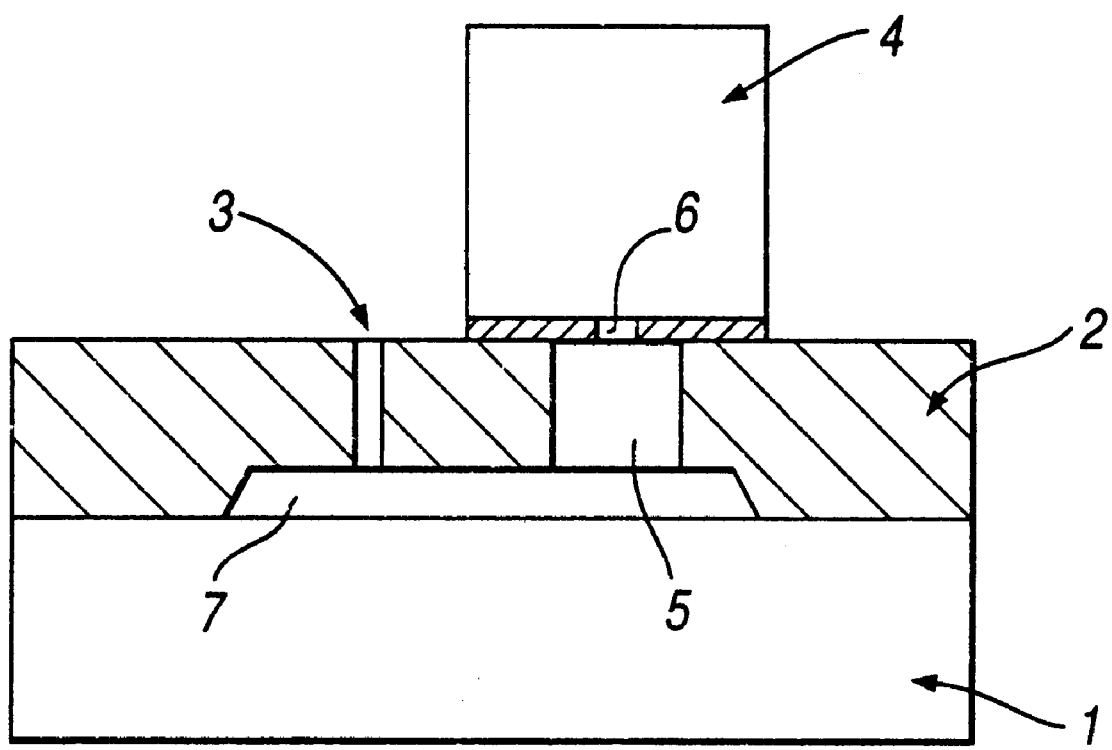

GAS SENSORS

BACKGROUND OF THE INVENTION

Field of the Invention

This invention concerns improvements in or relating to electrochemical, amperometric gas sensors, for example toxic gas sensors or oxygen sensors of the kind disclosed in UK Patents Nos 1,571,282 and 2,094,005.

It is common practice in the field of such sensors to incorporate gas controlling gas diffusion barriers employing capillary hole barriers, solid membrane barriers or Knudsen barriers, and one of the attendant potential problems associated therewith is their blockage through contamination. For example, in industrial environments it is not unusual for diffusion barriers to become fouled or filled by overpainting, with water through washing down, with mud or other extraneous performance-inhibiting matter. Such fouling is not uncommon and it has been known for instruments to be dropped down manholes or into pits for example where they encounter water or mud with the damaging consequences indicated above.

The blocking of a diffusion barrier obviously affects the performance of the sensor. In the case of an oxygen sensor, the effect is that it fails safe by virtue of a decay in the signal resulting from oxygen starvation and accordingly a low oxygen alarm will be given. In complete contrast, however, with a toxic gas sensor fouling of the diffusion barrier will result in a fail dangerous situation since any toxic gas in the ambient air will no longer be able to access the sensor and will not therefore be detected. Examples of toxic gases which are commonly detected with electrochemical amperometric gas sensors are, carbon monoxide, hydrogen sulphide, sulphur dioxide, nitric oxide, nitrogen dioxide, chlorine and others.

SUMMARY OF THE INVENTION

An object of the present invention is thus to provide an improved sensor for detecting both toxic gas and oxygen levels which obviates the disadvantage attaching to conventional sensors.

According to the present invention, in a combined toxic gas sensor and an oxygen sensor including diffusion barriers, the oxygen sensor is mounted such that its diffusion barrier communicates with the downstream side of the diffusion barrier of the toxic gas sensor.

The diffusion barriers are of the capillary hole type as a preference, but it is to be understood that other types of barrier, for example solid membrane barriers or Knudsen barriers, may be employed. It is to be understood that the diffusion barrier of one of the sensors may be different from that of the other sensor.

In this arrangement the oxygen sensor is so placed as to monitor the oxygen concentration within the region between the toxic gas sensor diffusion barrier and its sensing electrode. The toxic gas diffusion barrier will normally present no significant restriction to the ingress of oxygen from the ambient air and the oxygen sensor can function in its normal way to detect oxygen deficiency in the ambient air.

In practice, there will be some reduction in the oxygen signal given by the relationship:

$$\frac{1}{S} = \frac{1}{SO} + \frac{1}{ST}$$

where S is the oxygen sensor signal in position on the toxic gas sensor, SO is the oxygen sensor signal with its diffusion barrier open to the air and ST would be the oxygen sensor signal inside the toxic gas sensor without its own controlling barrier. ST is usually very much greater than SO and therefore S tends to SO. However, even if ST were a significant series diffusion barrier compared to SO, the oxygen sensor signal could be easily calibrated in the assembled condition and the toxic gas sensor barrier check and oxygen deficiency functions would operate as described for this invention.

In the event that the toxic sensor diffusion barrier becomes blocked, the oxygen sensor will consume any oxygen within the internal space of the toxic sensor. As a result the oxygen sensor signal will decline and eventually an oxygen deficiency alarm will be initiated. In order to differentiate unambiguously between a blocked diffusion barrier on the toxic gas sensor and a genuine oxygen deficiency condition in the ambient environment, a second oxygen sensor with its capillary diffusion barrier open directly to the external environment may be provided. However, in the absence of a second oxygen sensor, a fail-safe alarm will be given in the event of either a low oxygen condition or a blocked diffusion on the toxic gas sensor.

Any suitable means may be provided for securing the sensors together to form a modular unit.

BRIEF DESCRIPTION OF THE DRAWING

By way of example only, one embodiment of a combined toxic gas sensor and an oxygen sensor according to the invention is described below with reference to the accompanying drawing which is a schematic partial view of such a combination showing part thereof in section.

DETAILED DESCRIPTION OF THE PREFERRED EMBODIMENT

Referring to the drawing, a conventional toxic gas sensor, such for example as is disclosed in UK Patent No 2 094 005, includes a body 1 which has a top plate 2, shown in section, secured to its relatively upper face. The manner of securement of the plate 2 to the sensor body 1 is not shown in the drawing but may be selected from any of the conventional means known in the art, such as bolting, crimping using outer metal envelopes, ultrasonic welding, or 'snapfits' or any other suitable means.

The top plate 2 has a controlling diffusion barrier 3 which determines the sensitivity response of the sensor to the toxic gas as described for example in UK Patent No 1 571 282. The diffusion barrier communicates from the ambient air, through the top plate 2 into a cavity 7 which may optionally be filled with a porous chemical filter material for removing cross interfering gases as described in U.S. Pat. No. 4,633,704.

The toxic gas to be sensed diffuses through the cavity and any filter material present with no significant diffusion resistance, compared to the diffusion barrier 3, to the sensing electrode located in the sensor body 1 where it reacts to generate a signal current proportional to the gas concentration. Within the sensor body 1 under the sensing electrode is located the usual and requisite components for the toxic gas sensor as described for example in UK Patent No 2 094 005, namely counter electrode, reference electrode (optional), separators, electrolyte and other elements which the skilled addressee will recognise as being necessary for the operation of the sensor.

The sensor may optionally incorporate additional, auxiliary electrodes as described for example in EP 0126623.

In the embodiment shown, the top plate 2 has an oxygen sensor 4 mounted on its outer surface. The sensor 4 has an inlet 6 communicating through a relatively large aperture 5 into the cavity 7. The sensor 4 may be a conventional amperometric, diffusion-controlled type known to those skilled in the art and as described for example in UK Patent No 1 571 282. The inlet 6 is a controlling diffusion barrier of the oxygen sensor 4 and is a capillary hole, but other types of controlling diffusion barrier may in the alternative be employed in the invention, for example solid membranes of Knudsen barriers.

Reference is made to 'Techniques and Mechanisms in Gas Sensing' by B S Hobbs, A D S Tantram, R Chan-Henry, editors P T Moseley, J W Norris, and D E Williams, 1991 (ISBN No 0-7503-0074-4).

The method of attachment of oxygen sensor 4 to the top plate 2 is not shown but can be of any suitable design that can achieve a gas tight seal between the oxygen sensor 4 and the top plate. It is important that the oxygen supply pathway to the sensor 4 is predominantly, if not exclusively, through the toxic gas sensor diffusion 3 and the cavity 7. The cavity 7, with any filter material present, and the aperture 5 should present only minimal diffusion resistance to oxygen accessing the oxygen sensor compared to the oxygen sensor controlling barrier 6 and the toxic sensor diffusion barrier 3.

Current collection and signal output connections, namely output pins to the control and measurement circuits, for the oxygen and toxic gas sensors are not shown and can be of any convenient form as used in the art of gas measurement with electrochemical sensors.

In operation the instruments of fixed detection installations incorporating such sensors as described herein are first subjected to a calibration and check routine with test gases. The functioning of the toxic gas sensor, including its diffusion barrier 3, would be tested and calibrated by exposing the sensor to a test gas containing a known concentration of the toxic gas to be measured when in service. The oxygen sensor test and calibration would be conducted in clean air. In the alternative, the toxic gas sensor and the oxygen sensor could be tested and calibrated simultaneously using a test gas composed of toxic gas and oxygen at known concentrations with a suitable balance gas such as nitrogen. Conveniently this test gas could comprise a known concentration of toxic gas in clean air. Some toxic gases such as nitric oxide, however, cannot be stored in pressurised gas cylinders in the presence of oxygen due to chemical reaction with the oxygen. In the case of nitric oxide for example, the nitric oxide reacts with oxygen becoming converted to nitrogen dioxide. In such cases the testing and calibration would need to be carried out with separate anaerobic mixtures of the toxic gas and clean air.

Another test that could be conducted during the calibration and check routine would be to measure the oxygen sensor output with a simple block on the toxic gas sensor controlling diffusion barrier 3 to confirm that any oxygen leaks to the oxygen sensor 4 are insignificant, relative to the diffusion pathway through the toxic gas sensor diffusion barrier, and also to confirm the level to which the output from the oxygen sensor 4 would reduce in the event of a full blockage of the toxic sensor diffusion barrier inlet.

In service the calibrated and checked sensor would provide an oxygen measurement from the oxygen sensor 4 given by the reciprocal relationship set forth supra. The instrument output would have been set during the calibration routine to read 20.9% oxygen in air. In the event that the controlling diffusion hole 3 becomes blocked either partially or completely, then the oxygen sensor 4 would reduce accordingly and the instrument would produce an alarm. Similarly, the oxygen sensor 4 would reduce and an alarm produced in the event of a reduced oxygen concentration level in the external ambient, even though the controlling diffusion hole 3 were not blocked. In order to avoid any ambiguity due to these two alternative alarm conditions, a second oxygen sensor may be employed to monitor external ambient oxygen levels. Where two oxygen sensors are provided, to avoid the pair running continuously, the second external sensor could be switched off and only activated if the internal sensor indicated a reduced oxygen concentration. In this way the instrument would be able to differentiate between a blocked toxic sensor diffusion barrier and genuine oxygen deficiency condition in the external ambient.

We claim:

1. A combined toxic gas sensor including a diffusion barrier and an oxygen sensor including a diffusion barrier wherein the oxygen sensor is mounted such that the diffusion barrier of the oxygen sensor only communicates with the downstream side of the diffusion barrier of the toxic gas sensor.

2. A combined toxic gas sensor and an oxygen sensor according to claim 1 in which the diffusion barrier of one sensor consists of capillary holes and the diffusion barrier of the other sensor consists of a solid membrane.

3. A combined toxic gas sensor and an oxygen sensor according to claim 1 in which the diffusion barrier of one sensor consists of capillary holes and the diffusion barrier of the other sensor consists of a Knudsen barrier.

4. A combined toxic gas sensor and an oxygen sensor according to claim 1 in which a further oxygen sensor is included and is fixed externally of the toxic gas sensor.

5. A combined toxic gas sensor and an oxygen sensor according to claim 1 in which the oxygen sensor is releasably mounted on the toxic gas sensor.

6. A combined toxic gas sensor and an oxygen sensor according to claim 1 in which the toxic gas sensor and oxygen sensor each includes a sensor body enclosing a sensing electrode, a counter electrode, a chamber for containing an electrolyte, wicking arrangements for providing an electrolytic connection between the electrodes, and current collecting means associated with the sensing and counter electrodes.

7. A combined toxic gas sensor including a diffusion barrier comprising capillary holes and an oxygen sensor including a diffusion barrier comprising capillary holes wherein the oxygen sensor is mounted such that the diffusion barrier of the oxygen sensor only communicates with the downstream side of the diffusion barrier of the toxic gas sensor.

8. A combined toxic gas sensor including a diffusion barrier comprising a solid membrane and an oxygen sensor including a diffusion barrier comprising a solid membrane wherein the oxygen sensor is mounted such that the diffusion barrier of the oxygen sensor only communicates with the downstream side of the diffusion barrier of the toxic gas sensor.

9. A combined toxic gas sensor including a diffusion barrier comprising a Knudsen barrier and an oxygen sensor including a diffusion barrier comprising a Knudsen barrier wherein the oxygen sensor is mounted such that the diffusion barrier of the oxygen sensor only communicates with the downstream side of the diffusion barrier of the toxic gas sensor.

* * * * *